United States Patent [19]

Hermann et al.

[11] Patent Number: 5,135,472
[45] Date of Patent: Aug. 4, 1992

[54] NON-LINTING COMPOSITE GAUZE MATERIAL

[75] Inventors: Paul F. Hermann, Boothbay Harbor, Me.; Joel S. Wildstein, Ledyard; Henry B. Sprague, Stonington, both of Conn.

[73] Assignee: United Foam Plastics Corporation, Georgetown, Mass.

[21] Appl. No.: 758,168

[22] Filed: Sep. 11, 1991

Related U.S. Application Data

[63] Continuation of Ser. No. 489,379, Mar. 6, 1990, abandoned, which is a continuation-in-part of Ser. No. 13,255, Feb. 9, 1987, abandoned.

[51] Int. Cl.⁵ .................. B32B 27/00; B32B 27/40; A61L 15/00; A61F 13/00
[52] U.S. Cl. ..................... 602/41; 424/446; 428/425.1; 428/507
[58] Field of Search .............. 604/304, 307; 424/443, 424/446; 428/425.1, 507; 602/41, 42

[56] References Cited

U.S. PATENT DOCUMENTS

| | | | |
|---|---|---|---|
| 2,764,976 | 10/1956 | Skiles, Jr. et al. | 128/156 |
| 2,993,013 | 7/1961 | Wolfe, Jr. | 260/2.5 |
| 3,046,172 | 7/1962 | Reid | 154/46 |
| 3,254,357 | 6/1966 | Caul et al. | 15/118 |
| 3,317,367 | 5/1967 | Koller | 161/67 |
| 3,446,208 | 5/1969 | Fukuda | 128/156 |
| 3,805,532 | 4/1974 | Kistner | 61/36 |
| 3,968,060 | 7/1976 | Vincent et al. | 260/2.5 |
| 4,137,200 | 1/1979 | Wood et al. | 521/159 |
| 4,182,649 | 1/1980 | Isgur et al. | 162/101 |
| 4,192,827 | 3/1980 | Mueller et al. | 525/123 |
| 4,193,887 | 3/1980 | Stone et al. | 252/91 |
| 4,209,605 | 6/1980 | Hoy et al. | 528/54 |
| 4,323,656 | 4/1982 | Strickman et al. | 521/109 |
| 4,537,819 | 8/1985 | Schortmann et al. | 428/284 |
| 4,619,948 | 10/1986 | Kennedy et al. | 521/52 |
| 4,828,542 | 5/1989 | Hermann | 604/3 |
| 4,838,253 | 6/1989 | Brassington et al. | 128/156 |

FOREIGN PATENT DOCUMENTS

1092902 11/1967 United Kingdom.
2069327 8/1981 United Kingdom.

OTHER PUBLICATIONS

"American Cotton Handbook", Merrill et al., (1949), pp. 88-89.
"Surgical Sponges: A Cause of Granuloma and Adhesion Formation", Sturdy et al., Ann. of Surg. 165(1), (1967), pp. 128-134.
"Granulomatous Peritonitis Due to Cellulose Fibers . . .", Tinker et al., Presented at New York Surgical Society, (Jan. 9, 1974).
"Cellulose Granulomas . . .", Tinker et al., Presented at the 7th Annual Meeting of the Alimentary Track, (May 25-26, 1978).
"Internal Overhealing: The Problem of Intraperitoneal Adhesion", Ellis, World J. of Surg. 4, (1980), pp. 303-306.
"Postoperative Adhesions: Etiology, Prevention, and Therapy", Levinson et al., Clin. Obst. and Gyn. 23(4), (1980), pp. 1213-1220.
"Foam Systems", Saunders et al., Polyurethanes Chemistry and Technology, vol. XVI Part 2, pp. 7-26.

Primary Examiner—Randall L. Green
Assistant Examiner—Paul Prebilic
Attorney, Agent, or Firm—Testa, Hurwitz & Thibeault

[57] ABSTRACT

A durable hydrophilic substantially non-linting water absorbent drapable composite material useful as wound dressing comprises cellulose fibers coated with hydrophilic polymer. The cellulose fibers may be open weave cotton gauze. The hydrophilic polymer may comprise a polyurethane foam prepolymer, such as a toluene diisocyanate terminated polyethylene glycol, optimally containing a surfactant. Alternatively, the polymer may comprise a polyethylene oxide, a carboxymethyl cellulose, or a polyvinylpyrrolidone. The water to prepolymer weight ratio of the polyurethane embodiment preferably is within the range of from about 6:1 to about 400:1. The hydrophilic polymer may be a polyethylene oxide carboxymethyl cellulose mixture.

14 Claims, 2 Drawing Sheets

NON-LINTING COMPOSITE GAUZE MATERIAL

CROSS REFERENCE TO RELATED PATENT APPLICATIONS

This is a continuation of copending application Ser. No. 07/489,379, filed on Mar. 6, 1990, now abandoned, is a continuation-in-part of our copending U.S. Pat. application Ser. No. 013,255 filed Feb. 9, 1987, now abandoned. The disclosure of U.S. Pat. application Ser. No. 013,255 is hereby incorporated by reference.

BACKGROUND OF THE INVENTION

This invention relates to substantially lint-free cotton gauze. Specifically it relates to a durable hydrophilic substantially non-linting water-absorbent drapable composite material comprising hydrophilic polymer resin applied to cellulosic fiber materials.

Cotton gauze is manufactured from twisted cotton fiber which is cleaned, bleached and sterilized. During the cleaning and bleaching process the thread is exposed to chemical treatments and becomes associated with leftover starch, proteins, casein, and resins. These materials, plus small fibers, can fall out of cotton gauze to contaminate a wound. During surgery, they may enter and remain undetected in the body to cause granulomas or they may enter the vascular system to cause even more serious conditions.

The problem of linting has become a concern of the FDA in recent years. Measures are being considered by the FDA to set performance standards for gauze to contain the problem of linting. In its response to comments received on proposed regulations classifying 51 general and plastic surgery devices, the FDA stated: "FDA agrees that current literature indicates that there is no 'safe' level of particulate exposure for gauze for internal use." 53(122) Fed. Reg. 23,867 (1988). It further stated, "FDA believes that a performance standard is necessary to control the design and construction of the [gauze], to reduce oarticulate matter contamination. and to assure adequate radiopacity." [emphasis added]53(122) Fed. Reg. 23,866 (1988). Thus, there is a recognized need for a substantially lint-free material to be used as a wound dressing material.

There is a serious problem of adhesion within a wound following any surgical operation. As one author stated, "[i]ntra-abdominal adhesions are now the most common cause of intestinal obstruction and the majority of adhesions are man-made." Ellis, "Internal Overhealing: The Problem of Intraperitoneal Adhesions", World J. of Surg., 4(3) 303-306 (1980). It has long been recognized that surgical gauze may be the source of such adhesions and granulomas. As early as 1966, it was stated, "[t]here is evidence that fragments of gauze introduced at operation may induce granulomata and deposition of fibrous tissue." Sturdy, et al., "Surgical Sponges: A Cause of Granuloma and Adhesion Formation", Ann. of Surg. 165(1) 128-134 (1967).

While cellulose gauze is hydrophilic, the cellulose fibers are not normally broken down by human enzyme systems. The chronic presence of such cellulose fibers remaining in a patient post-operation causes an immune reaction in the patient resulting in inflamation and adhesion. The problem is apparently worsened by use of woven cotton swabs, over use of nonwoven cotton swabs. See Levinson & Swolin, "Postoperative Adhesions: Etiology, Prevention, and Therapy", Clin. Obst. & Gyn., 23(4); 1213-1220 (1980).

There has been research into composite materials which may be used in place of cotton gauze. These materials are either less hydrophilic than gauze, less durable than gauze, or less drapable than gauze. The absorptive, hydrophilic nature of gauze is important since its primary function is as an absorbent material during surgery and wound healing. If the composite material is not durable, it will leave deposits of lint and such behind during the surgical procedure. Finally, the composite material must be drapable, or formable, to fit into spaces, such as an abdomen, during a surgical procedure. Thus, there is a need for a durable lint-free absorbent drapable composite material for use as a wound dressing material.

SUMMARY OF THE INVENTION

This invention involves wound dressing material which is substantially lint-free and highly water-absorbent. The composite material of this invention comprises an open weave cellulose fiber material, such as cotton gauze, coated with a hydrophilic polymer. Although coated with a polymer, the composite material is highly water-absorbent, drapable, elastic and non-toxic, thus suitable for use in place of conventional gauze during surgical procedures.

The wound dressing material of the invention comprises an open weave cellulose fiber material having warp and fill threads. These threads are coated with a hydrophilic polymer film, leaving interstitial regions open among the threads. The polymer is believed to specifically bind with the hydroxyl groups of the cellulose substantially to eliminate free particulate matter. The cellulose fiber material may be woven cotton gauze, and is useful as a wound dressing or during surgery. The polymer may be a polyurethane foam prepolymer applied to the gauze in aqueous solution. Alternatively, the polymer may be a polyethylene oxide, or carboxymethyl cellulose, or a polyvinylpyrrolidone. The preferred prepolymer is a toluene diisocyanate terminated polyethylene glycol, available as TREPOL ™ from Twin Rivers Engineering, Boothbay, ME. The prepolymer aqueous solution may contain a surfactant, such as Pluronic® F68, available from BASF, to assure wetting. The polymer used to coat the cellulose fibers may be a blend of water to prepolymer in a ratio of from about 6:1 to about 400:1. This blend results in an increase in water absorbency, over untreated cotton gauze, usually in excess of 100 percent, and often in excess of 200 percent. The water absorbency of polymer-coated cellulose fibers of the invention can be in the range of from about 300 to 450 percent (weight of absorbed water in 3-4.5 times weight of dry gauze), compared with the water absorbency of untreated cellulose fiber which absorbs u in the range of from about 200 to 250 percent.

It is an important aspect of the invention that the water to polymer ratio of the coating composition be sufficient effectively to bind particulate and resinous debris, without losing hydrophilicity, drapability or elasticity, and while maintaining an open weave structure. Thus, in view of this disclosure, skilled chemical engineers can manufacture the polymer-coated cellulose fiber material for use as wound dressing material.

It is an object of the invention to provide a substantially non-linting water-absorbent durable and drapable cotton gauze useful as a wound dressing.

This and other objects and features of the invention will be apparent from the description, drawings, and claims which follow.

BRIEF DESCRIPTION OF DRAWINGS

The foregoing and other objects of this invention, the various features thereof, as well as the invention itself, may be more fully understood from the following description, when read together with the accompanying drawings, in which.

Like reference characters in the respective drawn figures indicate corresponding parts.

DESCRIPTION

Figure 1:
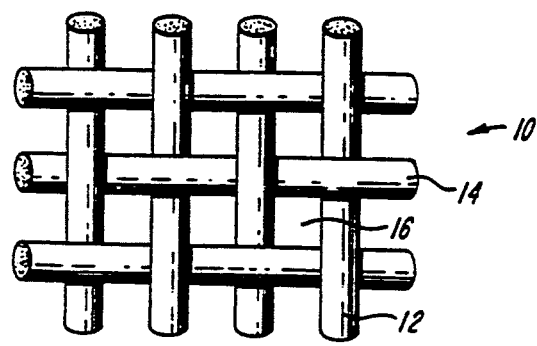
FIG. 1 illustrates the structure of an untreated section of woven cellulose fiber material showing warp and fill threads.

FIG. 1 depicts typical woven cotton gauze 10, having warp threads 12 and fill threads 14 which are interwoven defining interstitial regions 16 between the warps 12 and fills 14. The presence of such interstitial regions makes this material an open weave, which enhances its absorbency.

Each thread of cotton gauze 10 is a twisting of multiple cotton fibers 11. The chief constituent of cotton fiber 11 is cellulose. See Merrill, Macormac & Mauersberger, *American Cotton Handbook*, 88–89 (1949). The forces holding native cotton fiber together are hydrogen bonds between the hydroxyl groups in the cellulose. The structure of cotton fiber 11 is that of many anhydroglucose units joined by an oxygen bridge between the 1:4 carbons to give long cellulose chains. In addition to anhydroglucose, cotton fiber 11 also contains other materials such as proteins, waxes, and pectin. Thus, there is some particulate matter associated with natural cotton fiber. Cotton gauze 10, used primarily as a wound dressing, is manufactured from twisted cotton fiber which is cleaned, bleached and sterilized. During the cleaning and bleaching process the thread is exposed to chemical treatments including combinations of acids, enzymes, alkalies, soda, sodium silicate, chlorine, sodium hydroxide, sulfuric acid, silicate of soda, turkey red oil or hydrogen peroxide.

Figure 2:
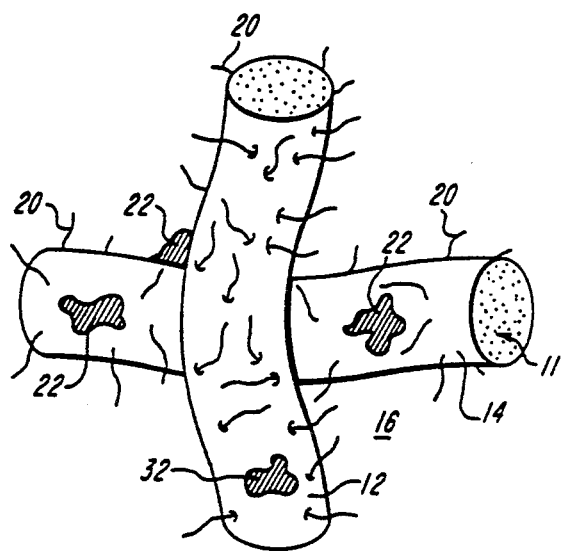
FIG. 2 is a schematic detailed view the intersection of an untreated warp thread and an untreated fill thread showing unbound particulate and resinous debris.

Processing cotton fibers results in leftover starch proteins, casein, and resins. These materials, plus small ends of fibers, can fall out of cotton gauze during use. Unbound particulate cotton fiber matter 20 and resinous debris 22, depicted in FIG. 2, may be left behind in wounds when cotton gauze is used as wound dressing material, causing adhesion and granulomas.

Figure 3:
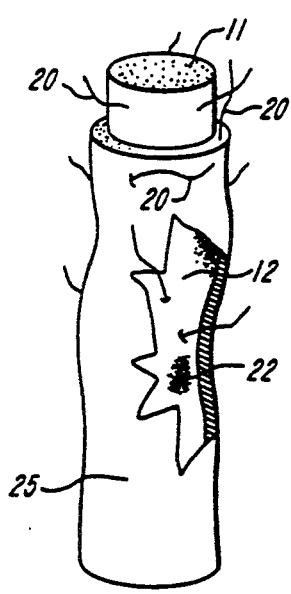
FIG. 3 is a schematic detailed, partially broken away view of a thread coated in accordance with the invention.
Figure 4:
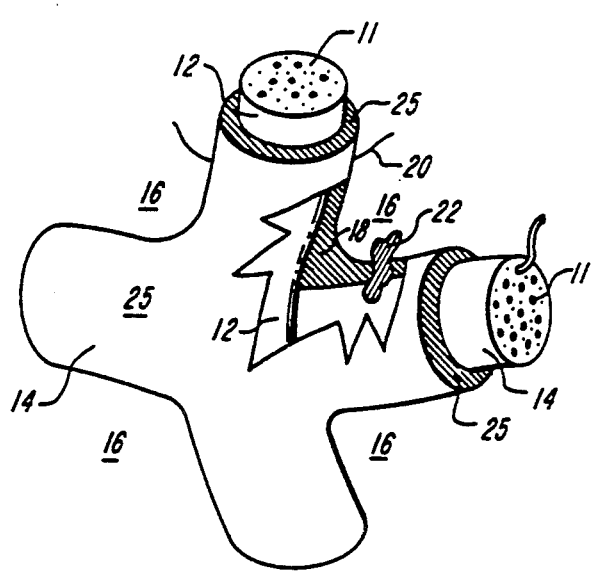
FIG. 4 illustrates an intersection of warp and fill threads, coated with the polymer in accordance with the invention.

As shown in FIG. 3, a polymer coating 25 may be used to cover the individual cotton warp threads and fill threads. FIGS. 3 and 4 depict how the polymer coating 25 binds particulate cotton fiber material 20 and resinous debris 22 in accordance with the invention. Notice from FIG. 4 that the interstitial space 16 is maintained open and is not filled in with the polymer coating 25. This is important in maintaining a high degree of absorptivity.

As shown in FIG. 4, the polymer coating produces polymer "fillets" 18 at the corner intersections of the warp 12 and fill 14 of the composite gauze material. The fillets 18 consist of the polymer connection at the junction of warp and fill threads. They enable the material to better maintain and conserve the open weave structure during use. In untreated cotton gauze, there is resistance to deformation in the longitudinal direction, however the gauze is readily tearable in the lateral direction. The presence of the fillets 18 enhances the tensile strength of the material.

The composite material is made by applying a thin film of hydrophilic polymer to preformed woven cellulose fiber material of the type shown in FIG. 1, i.e., conventional gauze. Cellulose has several free hydroxyl groups which may react with a hydrophilic polymer forming covalent bonds. The cellulose acts as a hydroxyl donor which can bond with an introduced polymer. The polymer system used to form the coating typically is a thermosetting prepolymer mixture dissolved in an aqueous vehicle which, when cross-linked, is not water soluble. The viscosity of the solution is important in achieving the thread-enveloping coating that maintains the open weave structure of the gauze. Viscosity and wettability of the coating solution is controlled in particular cases by adjusting the prepolymer/water ratio and blending with various surface active agents.

In one aspect of the invention, the treatment chemical is the prepolymer polyethylene oxide, available from Union Carbide. This polymer forms a good association with compounds such as carboxy methyl cellulose, and also is reactive toward a hydroxyl donor, such as cellulose. The polyethylene oxide may be mixed with the carboxy methyl cellulose at a ratio of 1:1. In one embodiment, polyethylene oxide and methyl cellulose are separately mixed at 6% by weight in water, then combined in a ratio of 1:1. The resulting solution is applied to the gauze. The solution cross-links, with irradiation, with the gauze and, in curing, forms an insoluble hydrophilic film on the individual threads thereof which retains free particulates. This composite material may absorb as much as 1400 times its weight in water or more. In another aspect of the invention, the treatment chemical is polyvinylpyrrolidone (see U.S. Pat. No. 4,192,827).

The currently preferred polymer is a hydrophilic polyurethane foam prepolymer applied from aqueous solution and then reacted in situ. The polyurethane foam may utilize any of a variety of urethane prepolymers normally employed for reaction to provide a reticulated, open cell foam. A preferred class of hydrophilic urethane prepolymers includes, for example, isocyanate terminated or capped polyoxyalkylene ethers including polyoxyethylene polyol prepolymers. Suitable prepolymers are described in U.S. Pat. No. 4,137,200 for "Cross Linked Hydrophilic Foams and Method"; U.S. Pat. No. 4,209,605 for "Process for Producing Shaped Polyurethane Hydrogel Articles"; U.S. Pat. No. 2,993,013 for "Cellular Polyurethane and Method of Preparing Same"; and U.S. Pat. No. 3,805,532. General procedures for the preparation of prepolymers are described by J. H. Saunders and K. C. Frisch in *Polyurethanes Chemistry and Technology*. Interscience Publishers, John Wiley & Sons, NY, Vol. XVI, Part 2, High Polymer Series, "Foam Systems" pages 7-26, and "Procedures for the Preparation of Prepolymers" pages 26 et seq.

The preferred prepolymer is TREPOL TM polyurethane prepolymer available from Twin Rivers Engineering, Route #27, Boothbay, ME, 04537. The TREPOL TM prepolymer is a polyisocyanate terminated polyethylene polyol with less than 6% available unreacted NCO groups and a component functionality of 2 or less. In another embodiment, HYPOL 3000 TM prepolymer may be used. HYPOL 3000 TM is a polyisocyanate capped polyoxyethylene polyol prepolymer having a reaction functionality of the prepolymer molecules greater than 2, and is available from W.R. Grace Company of New York.

Surface active agents may be added to the aqueous phase to adjust surface tension and to adjust wettability. The result is a hydrophilic structure which flows into voids within the cotton thread structure. Exemplary surfactants include: Schercopol OMS-N, a disodium monooleamido MEA sulfosuccinate, available from the Scher Chemicals, Inc., Industrial West, Clifton, NJ 07012; PPG 1025, a polypropylene glycol surfactant; Pluronic ® F68 or Pluronic ® P75, nonionic surfactants which are block copolymers of propylene oxide and ethylene oxide, available from BASF; or, Alcolec HS-3, an active combination of lecithin and sulfonated glycerides in an aqueous solution, available from American Lecithin Company, 32-34 61st Street, Woodside, Long Island, NY 11377.

The hydrophilic prepolymer is activated by the aqueous phase for polymerization upon mixing. Critical to this invention, the aqueous phase and the prepolymer are mixed together in a ratio by weight of aqueous phase to prepolymer sufficient to set an appropriate workable viscosity. For urethane embodiments, this ratio typically is in the range of from about 6:1 to about 400:1. The solution constitutes a flowable, liquid incipient polyurethane which subsequently cures in situ after adhering to the threads. The incipient foam is deposited on the open weave cellulose threads and excess water permeates the fiber. The use of hydrophilic urethane prepolymer in the ratio of from about 6:1 aqueous phase to prepolymer, to about 400:1 aqueous phase to Prepolymer can produce a coated product that is highly water absorbent and meets the physical characteristics of durability, flexibility and drapablility. The high water content of the mixture substantially eliminates foam formation when applied as a thin film to cotton gauze. The result is a polymer coating which is water absorptive in combination with the cotton substructure, but does not have discrete, well defined cells.

The excess water in the polymerization reaction mixture permits adjustment of viscosity to allow the resulting solution to be applied readily to the threads of the cotton gauze. This rheological property of the solution permits automated production. Excess water also helps to dissipate exothermic heat and to limit the temperature of the reaction. Finally, the excess water assures that all available isocyanate sites are consumed or reacted, assuming nontoxicity of the resulting composition.

Co-pending U.S. application Ser. No. 013,255 teaches a method of manufacturing composite materials by use of a machine illustrated in FIG. 5. The cotton gauze material with the incipient foamed resin of this invention can be manufactured using this type of equipment. In this process the aqueous resin coated gauze may be compressed to insure impregnation of the web with the resin and to establish the degree to which the polymer will occupy the interstitial regions of the fibers. Compression occurs at the adjustable nip of compression means 40, or between upper and lower parallel belts or conveyors of similar function (not shown). Alternatively, compression may occur between mold halves configured to impart shape to the surface of the composite material (not shown). In general, higher degrees of compression reduce the relative amount of incipient foam resin (lower foam density) and tend to promote greater preservation of voids among the fibers.

Figure 5:
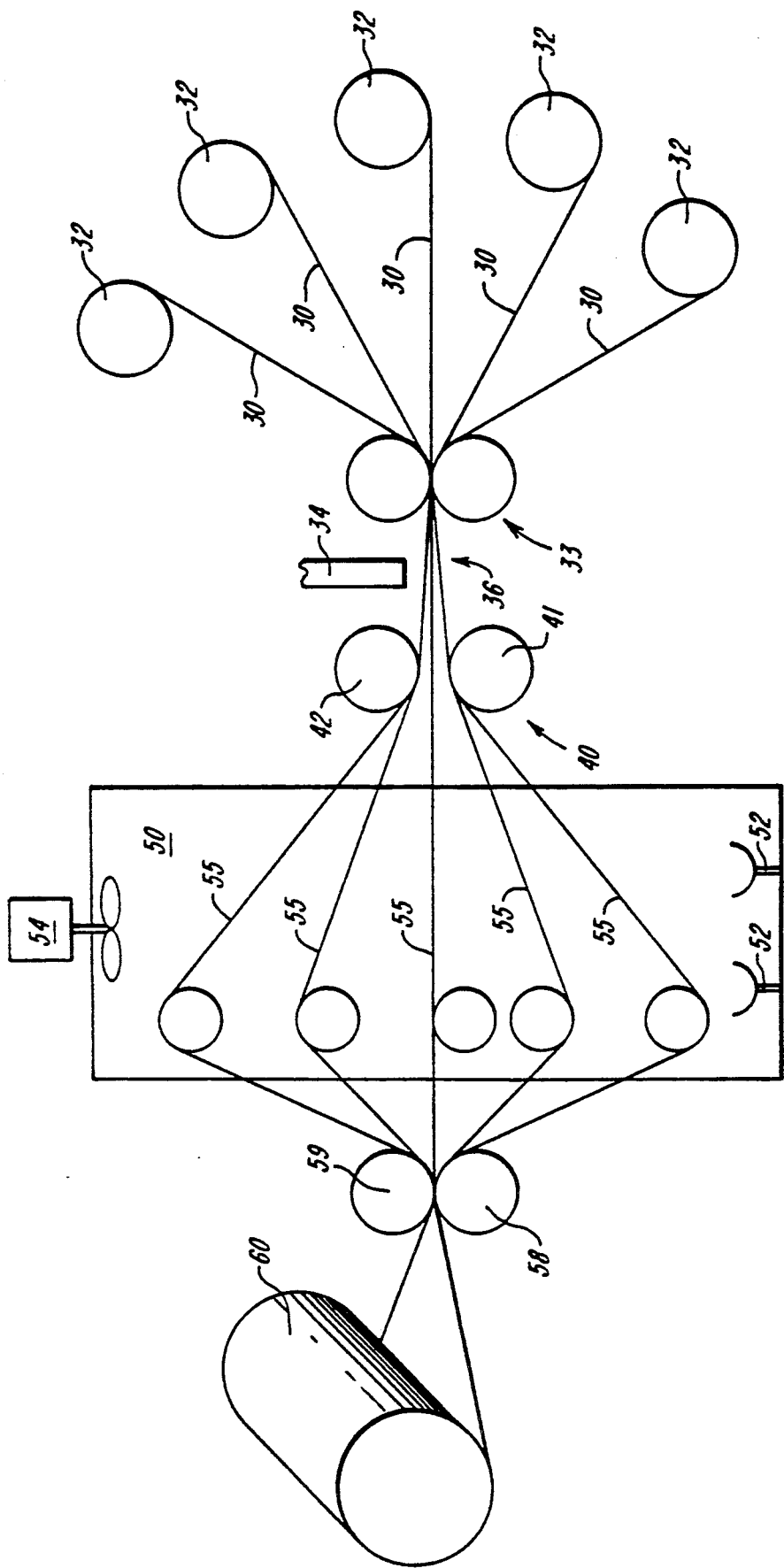
FIG. 5 is a schematic representation of a device for coating cellulose fiber material using the process of the invention.

FIG. 5 shows in schematic form the apparatus for performing the several steps of the method. The woven cotton gauze fibrous material 30 is unrolled from supply rolls 32 and is advanced horizontally. The individual sheets of material 30 pass through gathering means 33. Blended liquid polyurethane foam resin or other hydrophilic resin is dispensed from a blender/dispenser means 34 and is deployed over the surface of the material 30. The flowable, liquid incipient resin is allowed to penetrate the material 30 as the web advances.

The resin-coated material 36 is compressed by compression means 40 which may comprise, as is illustrated, an adjustable nip between a pair of compression rollers 41, 42. The compression means 40 further distributes and makes uniform the resin within the material 36 and, by compression of the material, establishes the relative quantity, and therefore density distribution, of incipient resin carried within the material, thereby controlling the degree to which the foam will occupy the interstitial regions among the fibers of the material.

The resin-coated material is then taken through a curing means 50 where completion of the polymerization and curing of the urethane takes place. The curing means 50 may include air heaters 52 or heated rollers (not shown) or both. The curing means 50 may also comprise an exhaust fan system 54. The polymer reaction and coating process may occur at room temperature. During and after curing, the composite material 55 may pass over separation rollers 56, which assists in keeping multiple sheets of composite material 55 separated during the curing process.

After curing, the composite material 55 may pass through a pair of drive rollers 58, 59 and onto a take-up roll 60. The drive rollers 58, 59 allow for multiple layers of composite material 55 to be combined into a single sheet for multi-layer gauze.

Cotton gauze may be treated, or coated, as it is unrolled from its storage roll, or may be treated in strips. Gauze also may be dipped in the polymer and massaged, rolled, or hung to dry. After extraction or evaporation of any liquid vehicles, which may be by room temperature or oven drying, the cured composite material may be cut to size or rolled as stock.

The invention will be further understood from the following non-limiting examples which constitute the best method currently known for practicing the invention.

Formulations of deionized water polyurethane foam prepolymer, and various surfactants were mixed in a laboratory mixer. A compressed roll of surgical gauze (Kendall), was dipped into the mixture, then immediately unrolled and hung to dry at room temperature in air. Each sample was assessed for its ability to hold fibers and cotton residues in place, and examined to determine whether the open weave structure of the gauze was maintained. Fiber and resin fallout were assessed by holding a 3"×3" piece of treated gauze between the palms of two hands held over a sheet of black glass. The hands were then rubbed together ten times, allowing any loose fibers and resin to fall onto the black-colored surface. The individual particles were then visually inspected and counted, without aid of a microscope.

In practice, the effectiveness of the gauze treatment may be tested by Putting test strips into boiling water and allowing the strip to be tossed around at a boil. The resulting effluent then may be passed through a particle counter, such as a Coulter-counter. In this manner, an accurate distribution of fibers and resin may be obtained, since each has a distinct size range. The various formulations tested and the results of each test are set forth below.

TABLE I

| Ex. | EG/HS-3 | H₂O | F68 | TREPOL ™ | Fiber fallout | Resin fallout |
|---|---|---|---|---|---|---|
| 1 | 0 | 400 | 0 | 1 | | many |
| 2 | 10.05 | 56.9 | 0 | 2 | 1 | many |
| 3 | 10.95 | 56.9 | 0 | 5 | few | many |
| 4 | 12 | 88 | 0 | 7 | 0 | 80 |
| 5 | 12 | 88 | 0 | 3 | 6 | 80 |
| 6 | 0 | 73.5 | 1.5 | 10 | closed gauze | |
| 7 | 0 | 88.2 | 1.8 | 10 | 7 | 30 |
| 8 | 0 | 93.1 | 1.9 | 5 | 18 | 80 |
| 9 | 0 | 99.5 | 0.5 | 30 | 0 | 3 |
| 10 | 0 | 99.5 | 0.5 | 12 | 0 | 0 |
| 11 | 0 | 99.5 | 0.5 | 12 | 0 | 20 |
| 12 | 0 | 99.5 | 0.5 | 5 | 1 | 2 |
| 13 | 0 | 99.5 | 0.5 | 2 | 8 | 30 |
| 14 | 0 | 99.5 | 0.5 | 1 | 2 | 25 |
| 15 | 0 | 99.5 | 0.5 | 0.5 | 16 | 20 |
| 16 | 0 | 99.5 | 0.5 | 0 | 58 | 50 |
| 17 | Untreated Gauze | | | | too many to count | |

EG/HS-3 is a mixture of two surfactants: Emulgade 100NI, supplied by Henkel Corporation, which is a mixture of cetearyl alcohol and ceteaseth-20; and Alcolec HS-3, an active combination of lecithin and sulfonated glycerides in aqueous solution, supplied by American Lecithin Company. Emulgade and HS-3 were each made into 2.5% aqueous solutions, then mixed together to form a 95% water solution (or 5% EG/HS-3 aqueous solution). F68 is Pluronic ® F68, a nonionic surfactant of block copolymers of propylene oxide and ethylene oxide, supplied by BASF. TREPOL ™ is a toluene diisocyanate terminated polyethylene glycol with less than 6% available unreacted NCO groups and a component functionality of 2 or less. It is available from Twin Rivers Engineering, Route 27, Boothbay, ME, 04537.

As illustrated by the data, the use of a surfactant, such as F68, may significantly decrease the amount of fiber and resin fallout. Examples 2-3 illustrate that varying amounts of prepolymer, in combination with surfactant EG/HS-3, does not affect resin fallout. In fact, as shown in Examples 4-5, varying the amount of F68 surfactant alone does not affect resin fallout.

Examples 6-8 illustrate various ratios of water to prepolymer, whereby lower prepolymer concentration results in "closed gauze". Closed gauze is gauze with filled interstitial regions. Examples 9-16 illustrate the effect of varying concentrations of prepolymer TREPOL ™ to water on fiber and resin fallout. As demonstrated by these examples, an optimal ratio of 99.5 parts water, 0.5 parts surfactant F68, and 12 parts prepolymer TREPOL ™ may result in a desired zero fiber fallout and zero resin fallout. Example 11 differs from example 10 in that air was blown through the coated gauze in Example 11 to open the windows in the gauze. As demonstrated by this example 11, this additional step renders the gauze treatment suboptimal.

The invention may be embodied in other specific forms.

What is claimed is:

1. A durable substantially lint-free water-absorbent drapable non-toxic composite material comprising:
   an open weave cellulose fiber material having warp threads and fill threads defining open spaces therebetween; and
   a hydrophilic polymer coating on said threads said coating comprising a polyurethane polymer having a thickness sufficient to leave said open spaces within said material bounded by said threads and serving substantially to prevent cellulose fiber loss from said threads during use of said material.

2. The material of claim 1 wherein said cellulose fiber material is woven cotton gauze.

3. The material of claim 1 wherein said polyurethane polymer is formed by reaction of a toluene diisocyanate terminated polyethylene glycol prepolymer.

4. The material of claim 1 wherein said composite material includes a surfactant.

5. The material of claim 4 wherein said surfactant is a hydrophilic poly-(oxyethylene-oxypropylene) polyol.

6. The material of claim 1 wherein said polyurethane polymer is the product of reaction of an aqueous prepolymer having a water to prepolymer ratio in the range of from about 6:1 to about 400:1.

7. The material of claim 6 wherein said composite material is characterized by a water absorbancy at least twice that of uncoated cellulose fiber material.

8. The material of claim 7 wherein said composite material is characterized by a water absorbancy 3-4.5 times that of uncoated cellulose fiber material.

9. A durable substantially lint-free water-absorbent drapable non-toxic composite material comprising:
   an open weave cellulose fiber material having warp threads and fill threads defining open spaces therebetween; and
   a hydrophilic polymer film coating on said threads, said coating comprising polyvinylpyrrolidone and being of a thickness sufficient to leave said open spaces within said material bounded by said threads and serving substantively to prevent cellulose fiber loss from said threads during use of said material.

10. A durable substantially lint free water absorbant drapable non-toxic composite material comprising:
    an open-weave cellulose fiber material having warp threads and fill threads defining open spaces therebetween; and
    a hydrophilic polymer film coating on said threads, said coating comprising a carboxy methyl cellulose polymer having a thickness sufficient to leave said open spaces within said material bounded by said threads and serving substantively to prevent cellulose fiber loss from said threads during use of said material.

11. A durable, substantially lint-free water-absorbent drapable non-toxic composite material comprising:
    an open weave cellulose fiber material having warp threads and fill threads defining open spaces therebetween; and
    a hydrophilic polymer film coating on said threads, said coating comprising a polyethylene oxide polymer having a thickness sufficient to leave said open spaces within said material bounded by said threads and serving substantially to prevent cellulose fiber loss from said threads during use of said material.

12. A durable substantially lint-free water-absorbent drapable non-toxic composite material comprising:
    an open weave cellulose fiber material having warp threads and fill threads defining open spaces therebetween; and
    a hydrophilic polymer coating on said threads comprising a water-soluble polymer which forms a hydrophilic continuous film having a thickness sufficient to leave said open spaces within said material bounded by said threads wherein the polymer coating allows water absorption by the material up to about 4.5 times greater than uncoated cellulose fiber material, and prevents cellulose fiber loss from said threads during sue of said materials.

13. The material of claim 12 wherein the cellulose fiber material comprises cotton gauze.

14. The material of claim 12 wherein the hydrophilic polymer coating is formed by reaction of a polyurethane prepolymer comprising toluene diisocyanate terminated polyethylene glycol with hydroxyl groups in the cotton gauze.

* * * * *